United States Patent [19]

Dickoré et al.

[11] Patent Number: 4,491,671
[45] Date of Patent: Jan. 1, 1985

[54] PROCESS FOR THE PREPARATION OF N-SUBSTITUTED IMIDO-DICARBOXYLIC ACID DIARYL ESTERS

[75] Inventors: Karlfried Dickoré, Leverkusen; Engelbert Kühle, Berg.-Gladbach, both of Fed. Rep. of Germany

[73] Assignee: Bayer Aktiengesellschaft, Leverkusen, Fed. Rep. of Germany

[21] Appl. No.: 387,096

[22] Filed: Jun. 10, 1982

Related U.S. Application Data

[63] Continuation of Ser. No. 233,247, Feb. 10, 1981, abandoned.

[30] Foreign Application Priority Data

Sep. 19, 1980 [DE] Fed. Rep. of Germany ....... 3035393

[51] Int. Cl.$^3$ .......................................... C07C 125/067
[52] U.S. Cl. ............... 560/115; 260/465 D; 549/426; 549/493; 560/22; 560/29; 560/31; 560/32; 560/133; 560/134; 560/137
[58] Field of Search .............. 260/465 D; 549/426, 549/493; 560/22, 29, 31, 32, 115, 133, 134, 137

[56] References Cited

U.S. PATENT DOCUMENTS

| | | | |
|---|---|---|---|
| 3,035,969 | 5/1962 | Hartle et al. | 560/132 X |
| 3,206,502 | 9/1965 | Heiss et al. | 560/132 |
| 3,393,224 | 7/1968 | Brookes et al. | 560/132 X |
| 3,789,033 | 1/1974 | Hagemann et al. | 560/132 X |
| 3,873,553 | 3/1975 | Hearsey | 560/132 X |
| 4,013,706 | 3/1977 | Anatol et al. | 560/115 X |
| 4,014,923 | 3/1977 | Kuhle et al. | 560/134 X |

Primary Examiner—Richard L. Raymond
Attorney, Agent, or Firm—Felfe & Lynch

[57] ABSTRACT

The present invention relates to a process for the preparation of N-substituted imido-dicarboxylic acid diaryl ester compound of the formula $$R^1-N(CO-OR^2)_2 \qquad (I)$$

wherein
  $R^1$ is an optionally substituted aliphatic, cycloaliphatic, araliphatic, aromatic or heterocyclic radical; and
  $R^2$ is an optionally substituted aryl radical, which are useful as intermediates for the production of known herbicides, which process comprises reacting a primary amine of the formula $$R^1-NH_2 \qquad (II)$$

with a carbonic acid aryl ester halide of the formula $$X-CO-OR^2 \qquad (III)$$

wherein X is a halogen atom, at a temperature between 100° and 300° C.

33 Claims, No Drawings

PROCESS FOR THE PREPARATION OF N-SUBSTITUTED IMIDO-DICARBOXYLIC ACID DIARYL ESTERS

This is a continuation of application Ser. No. 233,247, filed Feb. 10, 1981 abandoned.

This invention relates to a process for the preparation of N-substituted imido-dicarboxylic acid diaryl ester compounds, more specifically to a single stage process for such preparation. The ester compounds produced are valuable intermediates for the synthesis of herbicidally active compounds.

As claimed in applicants' co-pending U.S. Ser. No. 233,248 filed Feb. 10, 1981, now abandoned, (corresponding to German Patent Application No. P 30 06 226.1), it is possible to prepare N-substituted imido-dicarboxylic acid diaryl esters by reacting corresponding carbamic acid aryl esters with carbonic acid aryl ester halides, if appropriate in the presence of a diluent, at elevated temperatures (100° to 300° C.). The carbamic acid aryl esters required must be prepared from the corresponding primary amines in a separate process stage, by reaction with carbonic acid aryl ester halides or carbonic acid diaryl esters.

The present invention now provides a process for the production of an N-substituted imido-dicarboxylic acid diaryl ester of the general formula $$R^1-N(CO-OR^2)_2 \quad (I)$$

in which
R$^1$ represents an optionally substituted aliphatic, cycloaliphatic, araliphatic, aromatic or heterocyclic radical and
R$^2$ represents an optionally substituted aryl radical,
in which a primary amine of the general formula $$R^1-NH_2 \quad (II)$$

in which
R$^1$ has the abovementioned meaning, is reacted with a carbonic acid aryl ester halide of the general formula $$X-CO-OR^2 \quad (III)$$

in which
R$^2$ has the abovementioned meaning and
X represents a halogen atom, optionally in the presence of an additional diluent, at a temperature between 100° and 300° C.

The present invention further provides, as new compounds N-substituted imido-dicarboxylic acid diaryl esters of the general formula (I), as defined above, in which R$^1$ represents a neopentyl (=2,2-dimethylpropyl) radical and R$^2$ represents a 4-methylphenyl or 4-chlorophenyl radical or in which R$^2$ represents a phenyl radical and R$^1$ represents a methyl, 1,1-dimethylpropyl, 1,2,2-trimethylpropyl, 2,2-dimethylbutyl, 1-isopropyl-2-methylpropyl, 1-ethyl-pentyl, 1-methyl-octyl, allyl, 4-tert.-butylcyclohexyl, (4-methyl-cyclohexyl)-methyl, cyclohex-3-enylmethyl, 3,4-dimethyl-cyclohex-3-enyl-methyl, cyclododecanyl, cyclododecanyl-methyl, 2-(bicyclo[2.2.1]heptyl)-methyl, 6-(2,3,3a,4,5,6,7,7a-octahydro-4,7-methano-indenyl)methyl, 2-(1,2,3,4,5,6,7,8,8a,4a-decahydro-1,4:5,8-dimethano-naphthyl)-methyl, 2-chloroethyl, 3,3-dichloro-3-fluoropropyl, 3,3,3-trifluoro-propyl, 2,2-difluoropropyl, 2,2,2-trifluoro-1-methyl-ethyl, 6-chloro-hexyl, 2-methoxy-ethyl, 3-methoxy-propyl, 5-cyano-pentyl, 2-ethoxycarbonyl-ethyl, phenyl, 3,4-dichlorophenyl, benzyl, fur-2-yl-methyl or tetrahydropyran-2-yl-methyl radical.

It is to be described as surprising that the reaction according to the invention, which very probably proceeds via the intermediate stage of the corresponding carbamic acid aryl esters (R$^1$—NH—CO—OR$^2$), leads smoothly, and with high yields, to the desired imido-dicarboxylic acid diaryl esters of formula (I), since carbamic acid aryl esters do not react with carbonic acid aryl ester halides of formula (III) in the desired manner in the presence of an acid-binding agent: it is indeed known that N-substituted dialkyl imido-esters can be prepared by reacting N-substituted carbamic acid alkyl esters with carbonic acid alkyl ester chlorides in the presence of metallic sodium (see J. Amer. Chem. Soc. 69, 2616–2618 (1947)).

However, attempts to apply this method to the corresponding carbamic acid aryl esters fail completely. For example, neopentyl-carbamic acid phenyl ester reacts with carbonic acid phenyl ester chloride under the reaction conditions according to the state of the art to give exclusively neopentyl isocyanate and diphenyl carbonate.

Even with butyl-lithium as the acid-trapping agent, no neopentylimido-dicarboxylic acid diphenyl ester is formed. It is all the more surprising that the reaction according to the invention proceeds smoothly at elevated temperature and in the absence of an acid-trapping agent. According to the state of the art, it would have been expected that, at elevated temperature, total re-splitting of the carbamic acid aryl ester initially formed into isocyanate and phenol would take place (see Houben-Weyl: Methoden der organischen Chemie (Methods of Organic Chemistry), 4th Edition, Volume 8, page 127 (1952)).

If neopentylamine and carbonic acid phenyl ester chloride are used as starting substances, the course of the reaction for the production of compounds of the present invention is illustrated by the following equation:

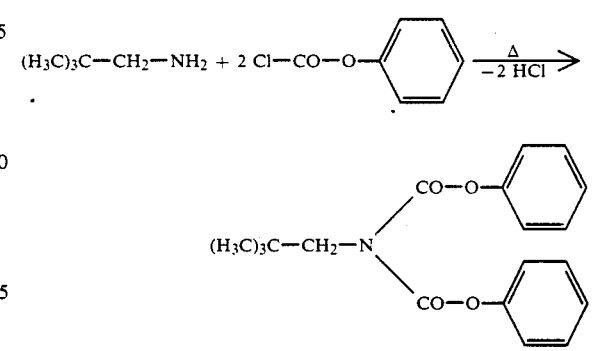

Preferred primary amines to be used as starting substances are those of formula (II) in which R$^1$ represents a straight-chain or branched alkyl radical which has 1 to 10 carbon atoms and is optionally substituted by lower alkoxy, lower alkylmercapto, halogen (in particular fluorine or chlorine), cyano or nitro; an alkenyl radical with 3 to 8 carbon atoms; an alkynyl radical with 3 to 8 carbon atoms; a cyclo-aliphatic ring which has 5 to 8 carbon atoms and is optionally substituted by lower alkyl; an araliphatic radical with a total of 7 to 12 carbon atoms, the aromatic ring system optionally being substituted by halogen, nitro, trifluoromethyl, cyano, lower alkyl and/or lower alkoxy; an aromatic radical which has 6 to 12 carbon atoms and is optionally substituted by halogen, nitro, trifluoromethyl, cyano, lower alkyl and/or lower alkoxy; or a heterocyclic radical with 5 or 6 ring atoms and 1 to 3 hetero-atoms, such as oxygen, sulphur and/or nitrogen, in the ring. The expressions "lower alkyl", "lower alkoxy" and "lower alkylmercapto" in the context of this invention are intended to denote appropriate radicals with in each case 1 to 4 carbon atoms.

The primary amines of the formula (II) which can be used according to the invention are already known, or they can be prepared by customary, known processes (see, for example, Houben-Weyl, Methoden der organischen Chemie (Methods of Organic Chemistry), 4th Edition, Volume XI/1, pages 9–1033 (1957)).

Specific examples of primary amines of the formula (II) which may be mentioned are: methylamine, ethylamine, propylamine, isopropylamine, 1,1-dimethyl-propylamine, 1,2-dimethyl-propylamine, 2,2-dimethyl-propylamine (neopentylamine), 1,2,2-trimethyl-propylamine, 1-ethyl-propylamine, 1-isopropyl-2-methyl-propylamine, butylamine, isobutylamine, sec.-butylamine, tert.-butylamine, 1-methyl-butylamine, 2,2-dimethyl-butylamine, 3,3-dimethyl-butylamine, 1,3,3-trimethyl-butylamine, pentylamine, 1-methyl-pentylamine, 2,2-dimethyl-pentylamine, 1,2,2-trimethyl-pentylamine, hexylamine, 2-ethylhexylamine, 1-methyl-octylamine, allylamine, 2-methylallylamine, propargylamine, cyclopropylamine, cyclopropyl-methylamine, cyclobutylamine, cyclopentylamine, cyclopentyl-methylamine, cyclohexylamine, cyclohexylmethylamine, 3-methyl-cyclohexylamine, 4-methyl-cyclohexylamine, 4-tert.-butyl-cyclohexylamine, 4-methylcyclohexyl-methylamine, 3,3,5-trimethyl-cyclohexylamine, cyclohex-3-enyl-methylamine, 3,4-dimethyl-cyclohex-3-enylamine, 3,4-dimethyl-cyclohex-3-enyl-methylamine, cycloheptylanylamine, cycloheptanyl-methylamine, cyclooctanylamine, cyclooctanyl-methylamine, cyclododecanylamine, cyclododecanyl-methylamine, adamantyl-methylamine, 2-(bicyclo[2.2.1-]heptyl)-methylamine, 6-(2,3,3a,4,5,6,7,7a-octahydro-4,7-methano-indenyl-methylamine, 2-(1,2,3,4,5,6,7,8,8a,-4a-decahydro-1,4:5,8-dimethanonaphthyl)methylamine, 5-(4,5,6,7,7a,3a-hexahydro-indenyl)-methylamine, 2-chloro-ethylamine, 2,2,2-trifluoro-ethylamine, 3,3-dichloro-3-fluoro-propylamine, 3,3,3-trifluoropropylamine, 2,2-difluoro-propylamine, 2,2,2-trifluoro-1-methyl-ethylamine, 6-chloro-hexylamine, 3-trifluoromethyl-cyclohexylamine, 4-trifluoromethyl-cyclohexylamine, 3-trifluoromethyl-cyclohexyl-methylamine, 4-trifluoromethyl-cyclohexyl-methylamine, 2-methoxyethylamine, 3-methoxy-propylamine, 5-cyano-pentylamine, 2-ethoxycarbonyl-ethylamine, aniline, 2-chloroaniline, 3-chloroaniline, 4-chloroaniline, 2,4-dichloroaniline, 3,4-dichloroaniline, 3,5-dichloroaniline, 2,4,5-trichloroaniline, 3-nitroaniline, 4-nitroaniline, 3-chloro-4-nitroaniline, 2-methylaniline, 2-chloro-6-methylaniline, 4-chloro-2-trifluoromethylaniline, 3-methylaniline, 3-trifluoromethylaniline, 4-methylaniline, 2,6-dimethylaniline, 2-ethylaniline, 2-ethyl-6-methylaniline, 2,6-diethylaniline, benzylamine, 1-phenyl-ethylamine, 2-phenyl-ethylamine, 2-chloro-benzylamine, 2,4-dichlorobenzylamine, fur-2-yl-methylamine, tetrahydro-fur-2-yl-methylamine, tetrahydro-pyran-2-yl-methylamine and tetrahydro-pyran-3-yl-methylamine.

Preferred carbonic acid aryl ester halides also to be used as starting substances are those of formula (III) in which $R^2$ represents a phenyl or naphthyl radical which is optionally substituted by chlorine, methyl and/or methoxy; and X represents a chlorine or fluorine atom.

The carbonic acid aryl ester halides of the formula (III) which can be used according to the invention are known, or they can be prepared by known processes. Thus, for example, the carbonic acid phenyl ester chlorides can be prepared in a manner which is in itself known, by phosgenation of phenols (see Houben-Weyl, Methoden der organischen Chemie (Methods of Organic Chemistry), 4th Edition, Volume 8, page 103 (1952)); the corresponding carbonic acid phenyl ester fluorides can be obtained analogously from phenols and difluorophosgene (see J.Chem. Soc. [London] 1948, page 2183).

Specific examples of starting compounds of the formula (III) which may be mentioned are: the carbonic acid ester chlorides of phenol, 4-chlorophenol, 4-cresol and 1-naphthol and the carbonic acid ester fluoride of phenol. A particularly preferred combination of starting compounds of formula (II) and (III) is neopentylamine hydrochloride and carbonic acid phenyl ester chloride.

The reaction according to the invention may be carried out using a diluent for the primary amine of formula (II).

It is appropriate to follow a procedure in which the carbonic acid aryl ester halide of formula (III) is initially introduced into the reaction vessel and is warmed to the reaction temperature, and a solution of the primary amine in a suitable diluent is slowly added. Suitable diluents for the amine to be added are low-boiling inert organic solvents, such as hydrocarbons and chlorinated hydrocarbons (for example petroleum ether, cyclohexane, methylene chloride, chloroform or difluorodichloro-methane, preferably petroleum ether (boiling range 30°–50°C.)); these solvents evaporate at the reaction temperature and thereby simultaneously serve as "entraining agents" for removal of the hydrogen halide formed.

It is also possible, and in many cases particularly advantageous, to carry out the reaction in an excess of the carbonic acid aryl ester halide of formula (III) used as a reactant, as the alternative to using the additional diluent.

The carbonic acid aryl ester halide of formula (III), which is in general initially introduced, can also be employed in the form of a dilute solution. Diluents which are suitable for this are high-boiling inert organic solvents, such as chlorinated or nitrated aromatic hydrocarbons (for example chlorobenzene, the dichlorobenzenes, the trichlorobenzenes or nitrobenzene). However, using such an additional diluent in general provides no noticeable advantage. It has proved to be more appropriate to carry out the reaction without such an additional diluent, and instead to employ the carbonic acid aryl ester halide of formula (III) in excess amounts.

If the reaction according to the invention is carried out without using an additional diluent for the (initially introduced) carbonic acid aryl ester halide of formula (III), up to 20 moles, but appropriately 4 to 15 moles and preferably 8 to 12 moles, of carbonic acid aryl ester halide can be employed per mole of a primary amine of the formula (II).

If a diluent is also used for the carbonic acid aryl ester halide of formula (III), in general 2 to 15, preferably 3 to 12, moles of carbonic acid aryl ester halide of formula (III) are employed per mole of the primary amine of formula (II). In the latter case, it is thus also advisable to employ the carbonic acid aryl ester halide of formula (III) in amounts which are greater than the stoichiometric amount.

The process according to the invention is carried out without the addition of an acid-binding agent. However, by using a low-boiling, inert organic solvent as the diluent for the primary amine, it is possible for a large proportion of the hydrogen halide formed in the course of the reaction to be removed from the reaction mixture, since, as mentioned above, the solvent simultaneously serves as an "entraining agent". In order to expel all of the hydrogen halide formed, it is advisable additionally to pass a continuous stream of air or nitrogen through the reaction mixture (see the Preparative Examples).

The reaction temperatures can be varied within the substantial range, as indicated above, of between 100° and 300° C., preferably between 170° and 250° C.

The reaction according to the invention is in general carried out under normal pressure.

The reaction products are isolated in a simple manner by separating the reaction mixture by distillation. Solid, higher-melting imido-dicarboxylic acid diaryl esters can also be easily purified by recrystallization.

The new N-substituted imido-dicarboxylic acid diaryl esters (I) according to the present invention and the compounds produced by the process of the present invention can be used as intermediate products for the preparation of known herbicidal active compounds from the 1,3,5-triazine-2,4-(1H,3H)-dione series (see, for example, DE-OS (German Published Specification) No. 2,254,200 and U.S. Patent Specification No. 4,056,527).

According to a process which has not hitherto belong to the state of the art (and which is the subject of copending U.S. Ser. No. 233,250, filed Feb. 10, 1981, U.S. Pat. No. 4,356,024) 1,3,5-triazine-2,4-(1H,3H)-diones of the general formula

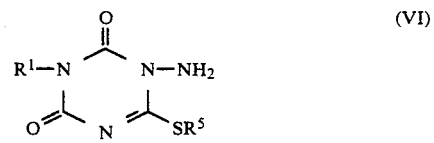

in which

R$^1$ has the abovementioned meaning and

R$^3$, R$^4$ and R$^5$ in each case represent identical or different alkyl radicals, can be prepared with a high yield and purity when the N-substituted imido-dicarboxylic acid diaryl esters according to the invention, of the general formula

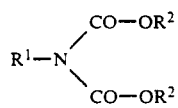

in which

R$^1$ and R$^2$ have the abovementioned meaning, are reacted with an isothiosemicarbazone of the general formula

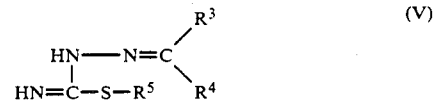

in which

R$^3$, R$^4$ and R$^5$ have the abovementioned meaning, in approximately stoichiometric amounts, without using a diluent and without adding a base as an auxiliary, at temperatures between 50° and 150° C., preferably between 70° and 120° C.

The triazinediones of formula (IV) can be worked up and isolated, for example, by a procedure in which the (optionally substituted) phenol formed in the condensation reaction—(I)+(V)→(IV)—is distilled off in vacuo and the residue is purified, if necessary, by distillation under a high vacuum or by recrystallization.

The 1,3,5-triazine-2,4(1H,3H)-diones of formula (IV) thus prepared are themselves herbicidal active compounds; however, they can also be easily converted into the corresponding 1-amino-1,3,5-triazine-2,4(1H,3H)-diones of the general formula

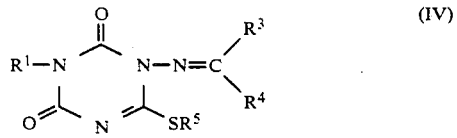

in which

R$^1$ and R$^5$ have the abovementioned meaning, which are likewise excellent herbicides, by hydrolytic splitting off of the alkylidene radical (=CR$^3$R$^4$) which serves as a protective group. Furthermore, the S-alkyl radicals (—SR$^5$) in compounds of formulae (IV) and (VI) can be replaced by alkylamino or dialkylamino groups by reaction with primary or secondary amines, herbicidal active compounds which are also known being obtained (see likewise DE-OS (German Published Specification) No. 2,254,200 and U.S. Patent Specification No. 4,056,527).

The new process given here for the preparation of the herbicidal active compounds of the general formulae (IV) and (VI) and 6-amino derivatives thereof, in which the imido-dicarboxylic acid diaryl esters of formula (I) according to the invention are used as starting compounds, has considerable and surprising advantages compared with the processes already known, for example from DE-OS (German Published Specification) No. 2,254,200. Thus, the cyclization reaction can be carried out in the melt of the starting materials without using solvents. No other auxiliaries, such as organic bases, are required in this procedure. The only by-products are phenols (no hydrogen halides being produced), which can be easily be separated off and re-used. Finally, the imido-dicarboxylic acid diaryl esters of formula (I) employed as starting substances can be prepared in high yields in an industrially simple manner from readily accessible precursors by the process claimed in the above-mentioned copending patent application.

The isothiosemicarbazones of the general formula (V) are known or they can be prepared by known processes, for example by S-alkylation of thiosemicarbazones (see Houben-Weyl, Methoden der organischen Chemie (Methods or Organic Chemistry), 4th Edition, Volume 9, page 912).

The synthesis of the particularly effective herbicidal active compound 1-amino-6-ethylthio-3-neopentyl-1,3,5-triazine-2,4(1H,3H)-dione of formula (VIa) (see for example, Danish Patent Specification No. 136,067), starting from the compound N-neopentylimido-dicarboxylic acid diphenyl ester of formula (Ia) according to the invention, is described below by way of example; the course of the reaction can be represented by the following equation:

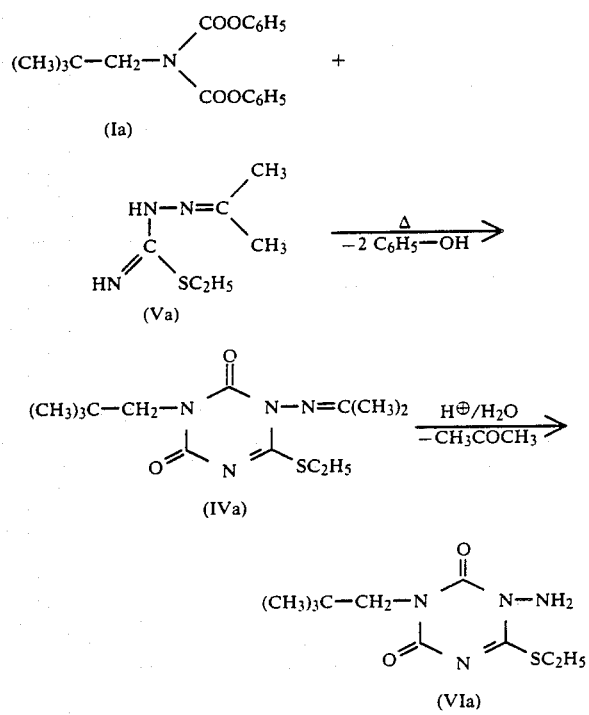

A mixture of 65.4 g (0.2 mole) of N-neopentylimidodicarboxylic acid diphenyl ester (see Preparative Example 1) and 31.8 g (0.2 mole) of acetone S-ethylisothiosemicarbazone of formula (Va) is melted and the melt is stirred at 100° C. for 5 hours. The phenol formed is then distilled off in vacuo. The residue, which essentially consists of 1-isopropylideneamino-6-ethylthio-3-neopentyl-1,3,5-triazine-2,4(1H,3H)-dione of formula (IVa), is dissolved in 200 ml of isopropanol. To split off the isopropylidene protective group hydrolytically, 2.8 g of p-toluenesulphonic acid are added, and 14.4 ml of water are added dropwise at a temperature of 60° C. and under a pressure of 200–300 mbar in the course of half an hour. The acetone formed is distilled off during the reaction, together with about 100 ml of isopropanol. The 1-amino-6-ethylthio-3-neopentyl-1,3,5-triazine-2,4(1H,3H)-dione of formula (VIa) which has crystallized out is filtered off at 0° C. and washed with methanol. 38.2 g of the compound of formula (VIa) of melting point 202° C. are obtained, corresponding to a yield of 74% of theory.

Herbicidally active 1-amino-3-isobutyl-6-methylthio-1,3,5-triazine-2,4(1H, 3H)-dione of formula (VIb), which is known (see, for example, Danish Patent Specification No. 130,067), can be prepared in an analogous manner starting from the compound N-isobutyl-imido-dicarboxylic acid diphenyl ester of formula (Ib) according to the invention, it being possible for the intermediate product 1-isopropylidene-amino-3-isobutyl-6-methylthio-1,3,5-triazine-2,4(1H,3H)-dione of formula (IVb) to be isolated:

1st stage:

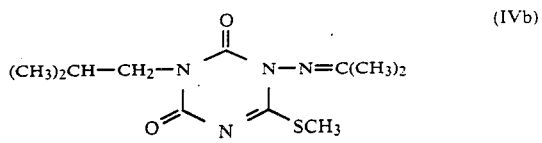

34.6 g (0.11 mole) of N-isobutyl-imido-dicarboxylic acid diphenyl ester of formula (IB) (see Preparative Example 5) and 16.0 g (0.11 mole) of acetone S-methylisothiosemicarbazone are melted at 50° C. and the melt is stirred for 4 hours in an oil bath of 100° C. The phenol formed is distilled off under a pressure of 18 mbars, the bath temperature being increased to 140° C. The residue (30.3 g) solidifies; it is boiled up with 150 ml of cyclohexane, 22.4 g of pure 1-isopropylideneamino-3-isobutyl-6-methylthio-1,3,5-triazine-2,4(1H,3H)-dione of formula (IVb) of melting point 125°–127° C. remaining as undissolved material. A further 6.4 g of the compound of formula (IVb) crystallize from the filtrate of the mixture. The total yield is 28.8 g (97% of theory). The compound of formula (IVb) can be distilled: boiling point: 165° C. under 0.38 mbar.

2nd stage

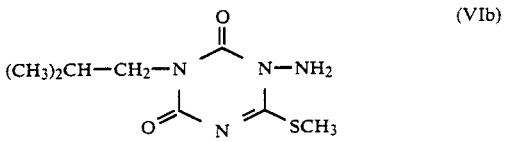

27.0 g (0.1 mole) of the compound of formula (IVb) are dissolved in 200 ml of isopropanol at 60° C. in a distillation apparatus and a pressure of 260 to 200 mbars is established, so that the solvent starts to boil and is condensed in the descending condenser. The internal temperature is 45°–50° C. A solution of 0.4 ml of concentrated sulphuric acid in 7 ml of water is then added dropwise in the course of 15 minutes, about 70 ml of isopropanol, together with the acetone formed, being distilled off during this period. 14.5 g of 1-amino-3-isobutyl-6-methylthio-1,3,5-triazine-2,4(1H,3H)-dione of formula (VIb) of melting point 167°–169° C. crystallize out, at 0° C., from the solution which remains; a further 4.5 g are obtained from the concentrated filtrate of the mixture. The total yield of 19.0 g corresponds to 83% of theory.

The Preparative Examples which follow illustrate the process of the present invention in more detail.

PREPARATIVE EXAMPLES

Example 1

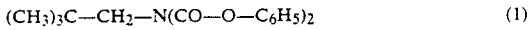

A 4 liter three-necked flask was provided with a stirrer and reflux condenser, to which a descending distillation bridge was connected via a Reitmeier attachment. A coarse-pored gas inlet frit was immersed as low as possible into the flask. A dropping funnel, with pressure compensation, was connected to the gas inlet frit via a ground glass joint. The gas inlet tube of the frit was connected to a nitrogen line and to a mercury bubbler. The reflux condenser was operated at 90°–100° C.

and the descending condenser at <20° C. All the ground glass connections before the frit were made secure towards excess pressure.

2.54 liters=3.13 kg (20 moles) of carbonic acid phenyl ester chloride were initially introduced and were heated to the reflux temperature, and a solution of 174.0 g (2 moles) of neopentylamine in 500 ml of petroleum ether was uniformly added dropwise into the gas inlet frit in the course of 8 to 9 hours, while stirring vigorously. In addition, a vigorous stream of nitrogen was passed through. The internal temperature was not allowed to exceed 185° C.; towards the end of the reactor a temperature of 189° to 190° C. was reached. Because of encrustation of the frit, a gauge pressure of up to 60 mm Hg (80 mbars) was established in the frit during the initial phase (5 to 30 minutes after the start of the dropwise addition), and finally fell to 10 to 15 mm Hg (about 13 to 20 mbars). The petroleum ether used was condensed in the descending condenser, together with some neopentyl isocyanate and a little carbonic acid phenyl ester chloride.

At the end of the dropwise addition period, the mixture was boiled under reflux for another hour, while passing further nitrogen through.

Analysis of this reaction solution by gas chromatography gave the following values, without taking into consideration the carbonic acid phenyl ester chloride employed in excess: 14.3% of diphenyl carbonate, 83.9% of N-neopentyl-imido-dicarboxylic acid diphenyl ester (1) and 0.7% of orthocarbonic acid tetraphenyl ester.

The resulting reaction solution was worked up by distillation: after separating off a small amount of first runnings, most of the excess carbonic acid phenyl ester chloride (boiling point: 76°–78° C./19 mbars) was distilled off, until the bottom temperature reached 140° C. 1.94 liters (=2.39 kg) of a 99.5% pure ester chloride, which could be re-used for the same reaction, were recovered in this manner.

Residual amounts of the carbonic acid phenyl ester chloride as well as the diphenyl carbonate were then distilled off under a high vacuum over a short Vigreux column, until a boiling point of 160° C. under 0.2 mbar was reached. 578 g of a residue which solidified and had a purity, determined by gas chromatography, of 98.5% were obtained, corresponding to a yield of 87% of theory of N-neopentyl-imido-dicarboxylic acid diphenyl ester (1); melting point 81° C. (from petroleum ether); boiling point: 156° C./0.02 mbar.

The compounds listed in the following Table were prepared in an analogous manner:

TABLE $$R^1-N(CO-OR^2)_2 \quad (I)$$

| Example No. | $R^1$ | $R^2$ | Melting point (°C.) | Boiling point (°C./mbar) |
|---|---|---|---|---|
| 2 | $CH_3-$ | $-C_6H_5$ | 102–105 | |
| 3* | $(CH_3)_2CH-$ | $-C_6H_5$ | 35–37 | 155/0.07 |
| 4* | $C_2H_5-CH(CH_3)-$ | $-C_6H_5$ | | 165–170/0.2 |
| 5* | $(CH_3)_2CH-CH_2-$ | $-C_6H_5$ | 40 | 160/0.1 |
| 6* | $(CH_3)_3C-$ | $-C_6H_5$ | 132 | 150/0.1 |
| 7 | $(CH_3)_3C-CH_2-$ | 4-$CH_3$-$C_6H_4$- | 71–73 | 172/0.008 |
| 8 | $(CH_3)_3C-CH_2-$ | 4-$Cl$-$C_6H_4$- | 72–73 | 182/0.03 |
| 9* | $(CH_3)_3C-CH_2-$ | naphthyl | 92–93 | |
| 10 | $C_2H_5-C(CH_3)_2-$ | $-C_6H_5$ | 95–97 | 150/0.05 |
| 11 | $(CH_3)_3C-CH(CH_3)-$ | $-C_6H_5$ | 40–42 | 159/0.15 |

TABLE-continued $$R^1-N(CO-OR^2)_2 \quad (I)$$

| Example No. | R¹ | R² | Melting point (°C.) | Boiling point (°C./mbar) |
|---|---|---|---|---|
| 12 | C₂H₅—C(CH₃)(CH₃)—CH₂— | —C₆H₅ | 49–50 | 178/0,05 |
| 13 | [(CH₃)₂CH—]₂CH— | —C₆H₅ | | 158–161/0,02 |
| 14 | C₄H₉—CH(C₂H₅)—CH₂ | —C₆H₅ | | 182–185/0,06 |
| 15 | C₇H₁₅—CH(CH₃)— | —C₆H₅ | | 173/0,09 |
| 16* | (C₂H₅)₂CH— | —C₆H₅ | 54–56 | 140/0,12 |
| 17 | CH₂=CH—CH₂— | —C₆H₅ | | 153/0,04 |
| 18* | cyclopentyl— | —C₆H₅ | 53 | 160/0,1 |
| 19* | cyclohexyl— | —C₆H₅ | 85 | 175/0,09 |
| 20 | (CH₃)₃C—cyclohexyl— | —C₆H₅ | | 186–200/0,001 |
| 21 | H₃C—cyclohexyl—CH₂— | —C₆H₅ | | 185–188/0,06 |
| 22 | cyclohexenyl—CH₂— | —C₆H₅ | | 195–200/0,09 |
| 23 | 1,2-dimethylcyclohexenyl—CH₂— | —C₆H₅ | | 200–205/0,07 |
| 24 | adamantyl— | —C₆H₅ | 57–62 | 210/0,6 |
| 25 | adamantyl—CH₂— | —C₆H₅ | | 240–250/0,1 |

TABLE-continued $R^1—N(CO—OR^2)_2$ (I)

| Example No. | $R^1$ | $R^2$ | Melting point (°C.) | Boiling point (°C./mbar) |
|---|---|---|---|---|
| 26 | [norbornyl-CH₂—] | $-C_6H_5$ | 84–86 | 202/0,02 |
| 27 | [tricyclic-CH₂—] | $-C_6H_5$ | 92–94 | |
| 28 | [tricyclic-CH₂—] | $-C_6H_5$ | | 232–240/0,07 |
| 29 | [tricyclic with double bond-CH₂—] | $-C_6H_5$ | | 215–220/0,07 |
| 30 | $Cl(CH_2)_2—$ | $-C_6H_5$ | | 177–190/0,1 |
| 31* | $F_3C—CH_2—$ | $-C_6H_5$ | 76 | 140/0,3 |
| 32 | $Cl_2FC—(CH_2)_2—$ | $-C_6H_5$ | 68–70 | 187/0,008 |
| 33 | $F_3C—(CH_2)_2—$ | $-C_6H_5$ | 66–69 | 147–153/0,3 |
| 34 | $CH_3—CF_2—CH_2—$ | $-C_6H_5$ | 60–62 | 160–164/0,08 |
| 35 | $F_3C—CH(CH_3)—$ | $-C_6H_5$ | | 150/0,17 |
| 36 | $Cl—(CH_2)_6—$ | $-C_6H_5$ | | 210/0,1 |
| 37 | $H_3C—O—(CH_2)_2—$ | $-C_6H_5$ | | 168/0,1 |
| 38 | $H_3C—O—(CH_2)_3—$ | $-C_6H_5$ | | 168–170/0,08 |
| 39 | $NC—(CH_2)_5—$ | $-C_6H_5$ | | 230–235/0,1 |
| 40 | $C_2H_5—O—CO—(CH_2)_2—$ | $-C_6H_5$ | | 190–193/0,08 |
| 41 | $C_6H_5—$ | $-C_6H_5$ | 124–125 | |
| 42 | [3,4-dichlorophenyl] | $-C_6H_5$ | 97–100 | |
| 43* | [3,5-dichlorophenyl] | $-C_6H_5$ | 178–180 | |
| 44 | $C_6H_5—CH_2—$ | $-C_6H_5$ | 70–72 | 191/0,01 |
| 45 | [furyl-CH₂—] | $-C_6H_5$ | | 190–200/0,1 |
| 46 | [tetrahydropyranyl-CH₂—] | $-C_6H_5$ | 78–79 | 176/0,007 |

The compounds labeled (*) have been described for the first time in copending U.S. Serial No. _____ (Bayer 4616), filed _____, corresponding to German patent Application P 30 06 226.1, the remaining compounds are new.

It will be understood that the specification and examples are illustrative, but not limitative, of the present invention and that other embodiments within t

What is claimed is:

1. Process for the production of an N-substituted imido-dicarboxylic acid diaryl ester compound of the formula $$R^1-N(CO-OR^2)_2 \quad (I)$$

wherein
- $R^1$ is an optionally substituted aliphatic, cycloaliphatic, araliphatic, aromatic or heterocyclic radical; and
- $R^2$ is an optionally substituted aryl radical, which process comprises reacting a primary amine of the formula
$$R^1-NH_2 \quad (II)$$

in which
- $R^1$ is defined as above with a carbonic acid aryl ester halide of the formula $$X-CO-OR^2 \quad (III)$$

in which
- $R^2$ is defined as above, and
- X is a halogen atom at a temperature between 185°–250° C. and in the presence of a low boiling inert organic solvent as a diluent,
said reacting step including introducing the carbonic acid ester halide of formula (III) into the reaction vessel; then
warming the carbonic acid ester halide (III) to said reaction temperature range; and
slowly adding a solution of the primary amine of formula (II) into the reaction flask at the reaction temperature.

2. Process as claimed in claim 1 wherein the diluent is a hydrocarbon.

3. Process as claimed in claim 1 wherein the diluent is a chlorinated hydrocarbon.

4. Process as claimed in claim 1 wherein the diluent is petroleum ether.

5. Process as claimed in claim 1 wherein the carbonic acid aryl ester halide of formula (III) is employed in a greater than stoichiometric amount.

6. Process as claimed in claim 1 wherein $R^1$ is alkyl of from 1 to 10 carbon atoms.

7. Process as claimed in claim 1 wherein $R^1$ is substituted alkyl wherein the substituents are selected from lower alkoxy, lower alkyl-mercapto, halogen, cyano or nitro.

8. Process as claimed in claim 1 wherein $R^1$ is alkenyl or alkynyl of from 3 to 8 carbon atoms.

9. Process as claimed in claim 1 wherein $R^1$ is cyalcoaliphatic with from 3 to 8 carbon atoms.

10. Process as claimed in claim 1 wherein $R^1$ is substituted cycloaliphatic wherein the substituents are selected from lower alkyl.

11. Process as claimed in claim 1 wherein $R^1$ is an araliphatic radical with from 7 to 12 carbon atoms.

12. Process as claimed in claim 1 wherein $R^1$ is a substituted araliphatic radical wherein the aromatic ring is substituted by halogen, nitro, trifluoromethyl, cyano, lower alkyl and lower alkoxy.

13. Process as claimed in claim 1 wherein $R^1$ is an aromatic radical of from 6 to 12 carbon atoms.

14. Process as claimed in claim 1 wherein $R^1$ is a substituted aromatic radical wherein the substituents are selected from halogen, nitro, trifluoromethyl, cyano, lower alkyl and lower alkoxy.

15. Process as claimed in claim 1 wherein $R^1$ is a heterocyclic radical with from 5 or 6 ring atoms and 1 to 3 hetero atoms.

16. Process as claimed in claim 1 wherein
$R^1$ is a straight chain or branched alkyl with from 1 to 10 carbon atoms; substituted alkyl, the substituents being selected from lower alkoxy, lower alkylmercapto, halogen, cyano or nitro; alkenyl or alkynyl with from 3 to 8 carbon atoms; a cycloaliphatic with from 3 to 8 carbon atoms; substituted cycloaliphatic wherein the substituents are selected from lower alkyl; an araliphatic with from 7 to 12 carbon atoms; a substituted araliphatic wherein the aromatic ring is substituted by halogen, nitro, trifluoromethyl, cyano, lower alkyl or lower alkoxy; an aromatic radical with from 6 to 12 carbon atoms; a substituted aromatic radical wherein the substituents are selected from halogen, nitro, trifluoromethyl, cyano, lower alkyl or lower alkoxy; a heterocyclic radical with from 5 or 6 ring atoms and 1 to 3 hetero-atoms.

17. Process as claimed in claim 1 wherein a carbonic acid aryl ester halide of formula $$X-CO-OR^2 \quad (III)$$

in which
- $R^2$ is a phenyl or naphthyl radical which is optionally substituted by chlorine, methyl or methoxy; and
- X is a chlorine or fluorine atoms, is employed.

18. Process as claimed in claim 1 wherein neopentylamine is reacted with carbonic acid phenyl ester chloride.

19. Process as claimed in claim 1 wherein sec.-butylamine is reacted with carbonic acid phenyl ester chloride.

20. Process as claimed in claim 1 wherein isobutylamine is reacted with carbonic acid phenyl ester chloride.

21. Process as claimed in claim 1 wherein neopentylamine is reacted with carbonic acid tolyl ester chloride.

22. Process as claimed in claim 1 wherein 2-aminohexane is reacted with carbonic acid phenyl ester chloride.

23. Process as claimed in claim 1 wherein 2,2-dimethyl-1-aminobutane is reacted with carbonic acid phenyl ester chloride.

24. Process as claimed in claim 1 wherein 2,4-dimethyl-3-aminopentane is reacted with carbonic acid phenyl ester chloride.

25. Process as claimed in claim 1 wherein 5-methylaminoheptane is reacted with carbonic acid phenyl ester chloride.

26. Process as claimed in claim 1 wherein 3-aminopentane is reacted with carbonic acid phenyl ester chloride.

27. Process as claimed in claim 1 wherein 3-amino-1-propylene is reacted with carbonic acid phenyl ester chloride.

28. Process as claimed in claim 1 wherein cyclopentylamine is reacted with carbonic acid phenyl ester chloride.

29. Process as claimed in claim 1 wherein cyclohexylamine is reacted with carbonic acid phenyl ester chloride.

30. Process as claimed in claim 1 wherein 2-methylaminobicyclo-[1,2,2]-heptane is reacted with carbonic acid phenyl ester chloride.

31. Process as claimed in claim 1 wherein 2,2,2-trifluoroethylamine is reacted with carbonic acid phenyl ester chloride.

32. Process as claimed in claim 1 wherein 1,1,1-trifluoro-2-aminopropane is reacted with carbonic acid phenyl ester chloride.

33. Process as claimed in claim 1 wherein the temperature is in the range of 185° C. to 190° C.

* * * * *